US007081468B2

(12) United States Patent
Krueger et al.

(10) Patent No.: US 7,081,468 B2
(45) Date of Patent: Jul. 25, 2006

(54) ORTHO-SUBSTITUTED ANTHRANILIC ACID AMIDES AND THEIR USE AS MEDICAMENTS

(75) Inventors: Martin Krueger, Berlin (DE); Andreas Huth, Berlin (DE); Orlin Petrov, Berlin (DE); Dieter Seidelmann, Berlin (DE); Karl-Heinz Thierauch, Berlin (DE); Martin Haberey, Berlin (DE); Andreas Menrad, Oranienburg (DE); Alexander Ernst, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/275,480

(22) PCT Filed: May 8, 2001

(86) PCT No.: PCT/EP01/05214

§ 371 (c)(1),
(2), (4) Date: Jun. 24, 2003

(87) PCT Pub. No.: WO01/85719

PCT Pub. Date: Nov. 15, 2001

(65) Prior Publication Data

US 2004/0102441 A1   May 27, 2004

(30) Foreign Application Priority Data

May 9, 2000   (DE)   ................ 100 23 486

(51) Int. Cl.
*A61K 31/44*   (2006.01)
(52) U.S. Cl. .................. 514/337; 514/313; 514/338; 514/357; 514/252.03; 544/235; 546/159; 546/283.1; 546/275.7; 546/330; 546/337

(58) Field of Classification Search ................ 546/337, 546/330, 275.7, 159, 283.1; 544/235; 514/313, 514/338, 357, 337, 252.03
See application file for complete search history.

(56) References Cited

U.S. PATENT DOCUMENTS 6,448,277 B1 *   9/2002   Altmann et al. ............ 514/357

FOREIGN PATENT DOCUMENTS

| WO | WO 0027819 | 5/2000 |
|---|---|---|
| WO | WO 0027820 | 5/2000 |

OTHER PUBLICATIONS

Strandtmann et al, J. Med. Chem. (1967), 10(6):1063-1065.*
Sofina et al. Experimental Evaluation of Antitumor Drugs in the USA and USSR and Clinical Correlations. NCI Monograph 55. NIH Publication No. 80-1933 (1980).*
Augustin, "Antiangiogenic tumour therapy: will it work?" *Trends in Pharmacological Sciences, Elsevier Trends Journal*, vol. 19, No. 6, Jun. 1, 1998, pp. 216-222, XP004145666.

* cited by examiner

*Primary Examiner*—Amelia A. Owens
(74) *Attorney, Agent, or Firm*—Millen, White, Zelano, Branigan, P.C.

(57) ABSTRACT

Ortho-substituted anthranilic acid amides and use thereof as pharmaceutical agents for treating diseases that are triggered by persistent angiogenesis are described.

4 Claims, No Drawings

ORTHO-SUBSTITUTED ANTHRANILIC ACID AMIDES AND THEIR USE AS MEDICAMENTS

This application is a 371 National Stage application of PCT/EP01/05214 filed May 8, 2001.

The invention relates to ortho-substituted anthranilic acid amides and their use as pharmaceutical agents for treating diseases that are triggered by persistent angiogenesis.

Persistent angiogenesis can be the cause of various diseases, such as psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases and arteriosclerosis or can result in an aggravation of these diseases.

Direct or indirect inhibition of the VEGF receptor can be used for treating such diseases and other VEGF-induced pathological angiogenesis and vascular permeable conditions, such as tumor vascularization. For example, it is known that the growth of tumors can be inhibited by soluble receptors and antibodies against VEGF.

Persistent angiogenesis is induced by the factor VEGF via its receptor. So that VEGF can exert this action, it is necessary that VEGF bind to the receptor, and a tyrosine phosphorylation is induced. Phenyl-anthranilamide derivatives that are used as angiotensin II-antagonists (EP 564 356) and as antiinflammatory agents and anti-ulcer compounds (U.S. Pat. No. 3,409,668) are already known.

It has now been found that compounds of general formula I,

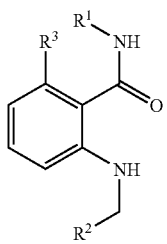

in which
R$^1$ stands for the group

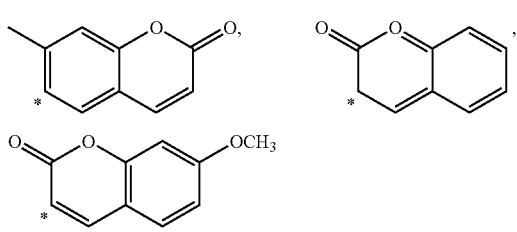

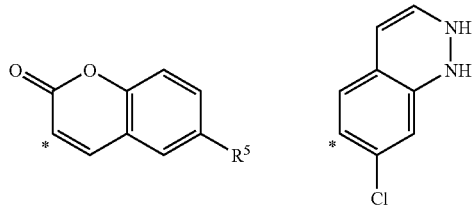

in which R$^5$ means chlorine, bromine or OCH$_3$,

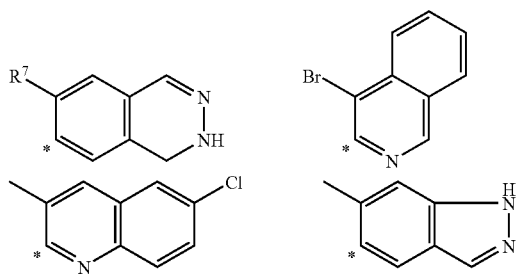

in which R$^7$ means CH3 or chlorine,

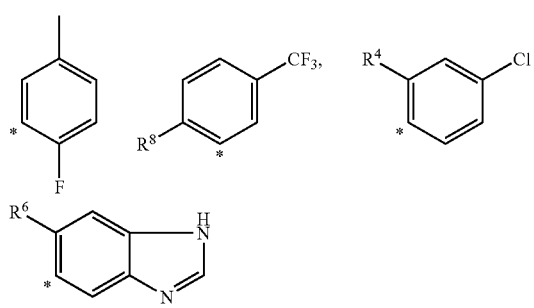

in which R$^4$ is fluorine, chlorine, bromine, —CF$_3$, —C≡N, CH$_3$—, —OCF$_3$ or —CH$_2$OH, R$^6$ is —CH$_3$ or chlorine, and R$_8$ is —CH$_3$, fluorine, chlorine, or —CF$_3$.

R$^2$ stands for pyridyl or the group

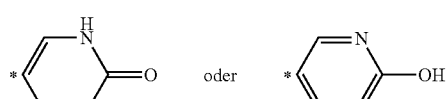

[Key: oder = or]

and
R$^3$ stands for hydrogen or fluorine,
as well as isomers and salts thereof, stop a tyrosine phosphorylation or the persistent angiogenesis and thus prevent the growth and propagation of tumors.

There are different tyrosine kinases (Web Site: S. Hauk, A. M. Quinn, Meth. in Enzymol. 1991, 200, 38–62, especially in the catalytic domains, subgroup PTK group XIV, Web page: http://www.sdsc.edu/Kinases/pkr/pk_catalytic/ pk_hanks_seq_align_long.html and McTigue et al., Structure 1999, 7, 319–330), which can be inhibited in a similar way. Thus, tyrosine kinase C, which occurs, i.a., in the stem cells, is also usually inhibited by compounds that inhibit VEGF (vascular endothelial growth factor). It is thus desirable to have compounds that inhibit VEGF selectively.

The compounds according to the invention are now specifically distinguished in that they have such selective properties and thus represent valuable compounds that prevent the growth and propagation of tumors.

The compounds of general formula I according to the invention also contain the possible tautomeric forms and include the E- or Z-isomers, or, if a chiral center is present, also the racemates and enantiomers.

The compounds of formula I as well as their physiologically compatible salts can be used as pharmaceutical agents based on their inhibitory activity relative to the phosphorylation of the VEGF receptor. Based on their profile of action, the compounds according to the invention are suitable for treating diseases that are caused by a persistent angiogenesis.

Since the compounds of formula I are identified as inhibitors of tyrosine kinases KDR and FLT, they are suitable in particular for treating such diseases that are caused by the persistent angiogensis that is triggered by the VEGF receptor or an increase in vascular permeability.

The subject of this invention is also the use of compounds according to the invention as inhibitors of tyrosine kinases KDR and FLT.

Subjects of this invention are thus also pharmaceutical agents for treating tumors or use thereof.

The compounds according to the invention can be used either alone or in a formulation as pharmaceutical agents for treating psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis and injuries to nerve tissue.

The compounds according to the invention can also be used in the inhibition of the reocclusion of vessels after balloon catheter treatment, in vascular prosthetics or after mechanical devices are used to keep vessels open, such as, e.g., stents.

In treating injuries to nerve tissue, a quick scar formation at the injury sites can be prevented with the compounds according to the invention, i.e., scars are prevented from forming before the axons are reconnected to one another. A reconstruction of the nerve compounds was thus facilitated.

The formation of ascites in patients can also be suppressed with the compounds according to the invention. VEGF-induced edemas can also be suppressed.

Such pharmaceutical agents, their formulations and uses, are also subjects of this invention.

The invention also relates to the use of the compounds of general formula I for the production of a pharmaceutical agent for treating tumors; psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, injuries to nerve tissue, inhibition of the reocclusion of vessels after balloon catheter treatment, in vascular prosthetics or after mechanical devices are used to keep vessels open, such as, e.g., stents.

To use the compounds of formula I as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions or emulsions. They also contain, moreover, adjuvants such as preservatives, stabilizers, wetting agents or emulsifiers, salts for changing osmotic pressure or buffers.

For parenteral administration, especially injection solutions or suspensions, especially aqueous solutions of the active compounds in polyhydroxyethoxylated castor oil, are suitable.

As carrier systems, surface-active adjuvants such as salts of bile acids or animal or plant phospholipids, but also mixtures thereof as well as liposomes or components thereof can also be used.

For oral administration, especially tablets, coated tablets or capsules with talc and/or hydrocarbon vehicles or binders, such as for example, lactose, corn starch or potato starch, are suitable. The administration can also be carried out in liquid form, such as, for example, as juice, to which optionally a sweetener is added.

The dosage of the active ingredients can vary depending on the method of administration, age and weight of the patient, type and severity of the disease to be treated and similar factors. The daily dose is 0.5–2000 mg, preferably 50–1000 mg, whereby the dose can be given as a single dose to be administered once or divided into 2 or more daily doses.

The above-described formulations and forms for dispensing are also subjects of this invention.

The production of the compounds according to the invention is carried out according to methods that are known in the art. For example, compounds of formula I are obtained, in that a) a compound of formula II

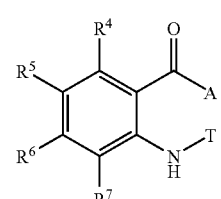

II

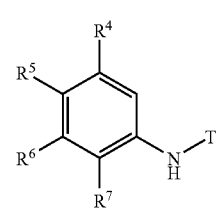

III

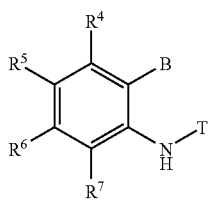

in which $R^4$ to $R^7$ have the above-mentioned meaning, and T is H or a protective group and A is halogen or $OR^{13}$, whereby $R^{13}$ means a hydrogen atom, $C_{1-4}$-alkyl or $C_{1-4}$-acyl, or closes a ring with T, is obtained by first having N be alkylated and COA then be converted into an amide and then having optionally protective groups be cleaved or converted first into the amide and then N-alkylated, or b) a compound of formula III in which $R^4$ to $R^7$ have the above-mentioned meaning, and T means H or a protective group, is obtained, in orthometallated form, and then is converted into an amide by being caught with an electrophile, then the protective group is cleaved and the amino group is alkylated, or c) a compound of formula IV in which $R^4$ to $R^7$ have the above-mentioned meaning, and T means H or a protective group, and B means halogen or O-triflate, O-tosylate or O-mesylate, is obtained by being converted into an amide, then the protective group being cleaved and the amino group being alkylated.

The sequence of steps can be reversed in all three cases.

The amide formation is carried out according to methods that are known in the literature.

For amide formation, it is possible to start from a corresponding ester. The ester is reacted according to J. Org. Chem. 1995, 8414 with aluminum trimethyl and the corresponding amine in solvents such as toluene at temperatures of 0° C. up to the boiling point of the solvent. This method can also be used in unprotected anthranilic acid esters. If the molecule contains two ester groups, both are converted into the same amide.

When nitriles are used instead of ester, amidines are obtained under analogous conditions.

For amide formation, however, all processes that are known from peptide chemistry are also available. For example, the corresponding acid can be reacted with the amine in HATU, preferably at room temperature, in aprotic polar solvents, such as, for example, dimethylformamide, via an activated acid derivative, that can be obtained, for example, with hydroxybenzotriazole and a carbodiimide, such as, for example, diisopropylcarbodiimide, or else with preformed reagents, such as, for example, HATU (Chem. Comm. 1994, 201) or BTU, at temperatures of between 0° C. and the boiling point of the solvent, preferably at 80° C. These methods can also be used in the unprotected anthranilic acids. For the amide formation, the process can also be used with the mixed acid anhydride, imidazolide or azide. A previous protection of the amino group, for example as amide, is not necessary in all cases but can advantageously affect the reaction. Isatoic acid anhydrides are a special starting material in which the protection of the amino group and the activation of the acid function exist at the same time.

If the amine is converted into the BOC-protected compound in advance, the ortho-position can be metallated by reaction with organometallic compounds, such as, for example, nbutyllithium, and then caught with isocyanates or isothiocyanates to form the anthranilamides or anthranilthioamides. A bromine or iodine substituent in this ortho-position facilitates the orthometallation by halogen-metal exchange. As a solvent, ethers such as diethyl ether or tetrahydrofuran or hydrocarbons such as hexane, but also mixtures thereof, are suitable. The addition of complexing agents such as tetramethylethylenediamine (TMEDA) is advantageous. The temperature ranges between −78° C. and room temperature. The cleavage of the BOC-amides is carried out by treatment with acids such as trifluoroacetic acid without solvent or in solvents such as methylene chloride at temperatures from 0° C. up to the boiling point of the solvent or with aqueous hydrochloric acid, preferably 1N hydrochloric acid, in solvents such as ethanol or dioxane at temperatures from room temperature up to the boiling point of the solvent.

The amide group can also be introduced by carbonylation. To this end, a start is made from the corresponding compounds of formula IV (o-iodine, o-bromine, or o-triflyloxyanilines), which are reacted with carbon monoxide at normal pressure or else elevated pressure and an amine in the presence of transition metal catalysts, such as, for example, palladium(II) chloride or palladium(II) acetate or else palladium tetrakis triphenylphosphine in solvents such as dimethylformamide. The addition of a ligand such as triphenylphosphine, and the addition of a base such as tributylamine can be advantageous (see, for example, J. Org. Chem. 1974, 3327; J. Org. Chem. 1996, 7482; Synth. Comm. 1997, 367; Tetr. Lett 1998, 2835).

If various amide groups are to be introduced into the molecule, for example, the second ester group must be introduced into the molecule after the first amide group is produced and then amidated, or one molecule is in one group as an ester while the other is present as acid, and the two groups are amidated in succession according to various methods.

Thioamides can be obtained from anthranilamides by reaction with diphosphadithianes according to Bull Soc. Chim. Belg. 87, 229, 1978 or by reaction with phosphorus pentasulfide in solvents such as pyridine or else without solvent at temperatures of 0° C. to 200° C.

The products can also be subjected to electrophilic aromatic substitutions as electron-rich aromatic compounds. Substitution is then carried out in ortho- or para-position in the amino group or one of the amino groups. Acylation can thus be carried out by Friedel-Crafts acylation with acid chlorides in the presence of Friedel-Crafts catalysts, such as, for example, aluminum trichloride in solvents such as nitromethane, carbon disulfide, methylene chloride or nitrobenzene at temperatures of between 0° C. and the boiling point of the solvent, preferably at room temperature.

According to processes that are known in the literature, one or more nitro groups can be introduced, for example, by nitrating acid, various concentrated nitric acids without solvent or by metal nitrates, such as, for example, copper(II) nitrate or iron(III) nitrate in polar solvents such as ethanol or glacial acetic acid or else in acetic anhydride.

The introduction of halogens is carried out according to processes that are known in the literature, e.g., by reaction with bromine, N-bromosuccinimide or N-iodosuccinimide or urotropin hydrotribromide in polar solvents, such as tetrahydrofuran, acetonitrile, methylene chloride, glacial acetic acid or dimethylformamide.

The reduction of the nitro group is performed in polar solvents at room temperature or elevated temperature. As catalysts for the reduction, metals such as Raney nickel or noble-metal catalysts such as palladium or platinum or else palladium hydroxide optionally on vehicles are suitable. Instead of hydrogen, for example, ammonium formate, cyclohexene or hydrazine can also be used in a known way. Reducing agents such as tin(II) chloride or titanium(III) chloride can also be used such as complex metal hydrides optionally in the presence of heavy metal salts. As reducing agents, iron can also be used. The reaction is then performed in the presence of an acid, such as, e.g., acetic acid or ammonium chloride, optionally with the addition of a solvent, such as, for example, water, methanol, iron/ammonia, etc. In the case of extended reaction time in this variant, an acylation of the amino group can occur.

If an alkylation of an amino group is desired, the amino group can be alkylated according to commonly used methods—for example with alkyl halides—or according to the Mitsunobu variant by reaction with an alcohol in the presence of, for example, triphenylphosphine and azodicarboxylic acid esters. The amine can also be subjected to a reductive alkylation with aldehydes or ketones, whereby the reaction can be performed in the presence of a reducing agent, such as, for example, sodium cyanoborohydride in a suitable inert solvent, such as, for example, ethanol, at temperatures from 0° C. up to the boiling point of the solvent. If a start is made from a primary amino group, a reaction can be carried out optionally in succession with two different carbonyl compounds, whereby mixed derivatives are obtained [Literature, e.g., Verardo et al. Synthesis (1993), 121; Synthesis (1991), 447; Kawaguchi, Synthesis (1985), 701; Micovic et al. Synthesis (1991), 1043]. It may be advantageous first to form the Schiff base by reaction of the aldehyde with the amine in solvents such as ethanol or methanol, optionally with the addition of adjuvants such as glacial acetic acid and then to add only reducing agent, such as, e.g., sodium cyanoborohydride.

The hydrogenation of alkene groups or alkine groups in the molecule is carried out in the usual way, for example, by catalytically activated hydrogen. As catalysts, heavy metals such as palladium or platinum, optionally on a vehicle or Raney nickel, can be used. As solvents, alcohols such as, e.g., ethanol, are suitable. The procedure is performed at temperatures from 0° C. up to the boiling point of the solvent and at pressures up to 20 bar, but preferably at room temperature and normal pressure. By using catalysts, such as, for example, a Lindlar catalyst, triple bonds can be partially hydrogenated into double bonds, whereby preferably the Z-form is produced.

The acylation of an amino group is carried out in the usual way, for example with an acid halide or an acid anhydride optionally in the presence of a base such as dimethylaminopyridine in solvents such as methylene chloride, tetrahydrofuran or pyridine, according to the SchottenBaumann variant in aqueous solution at weakly alkaline pH or by reaction with an anhydride in glacial acetic acid.

The introduction of the halogens chlorine, bromine, iodine or the azido group via an amino group can be carried out, for example, also according to Sandmeyer, by the diazonium salts that are intermediately formed with nitrites being reacted with copper(I) chloride or copper(I) bromide in the presence of the corresponding acid such as hydrochloric acid or hydrobromic acid or with potassium iodide.

If an organic nitrite is used, the halogens can be introduced, e.g., by adding methylene iodide or tetrabromomethane, into a solvent, such as, for example, dimethylformamide. The removal of the amino group can be achieved either by reaction with an organic nitrite in tetrahydrofuran or by diazotization and reductive boiling-down of the diazonium salt, for example, with phosphorus acid, optionally with the addition of copper(I) oxide.

Introduction of fluorine can be accomplished by, for example, Balz-Schiemann reaction of diazonium tetrafluoroborate or according to J. Fluor. Chem. 76, 1996, 59–62 by diazotization in the presence of HFxpyridine and subsequent boiling-down optionally in the presence of a fluoride ion source, such as, e.g., tetrabutylammonium fluoride.

The introduction of the azido group can be accomplished after diazotization by reaction with sodium azide at room temperature.

Ether cleavages are performed according to processes that are common in the literature. In this case, a selective cleavage can also be achieved in several groups that are present in the molecule. In this case, the ether is treated, for example, with boron tribromide in solvents such as dichloromethane at temperatures of between −100° C. up to the boiling point of the solvent, preferably at −78° C. It is also possible, however, to cleave the ether by sodium thiomethylate in solvents such as dimethylformamide. The temperature can be between room temperature and the boiling point of the solvent, preferably at 150° C.

The N-alkylation or O-alkylation of amides such as the pyrid-2-one or 2-hydroxypyridine can be accomplished according to methods that are known in the literature. Thus, an N-alkylation is achieved with bases such as sodium hydride or potassium carbonate in solvents such as dimethylformamide and alkylation with alkyl halides, such as methyl iodide, and an O-alkylation is achieved with bases such as silver carbonate in solvents such as tetrahydrofuran or toluene or preferably mixtures thereof with alkyl halides, such as methyl iodide. An O-alkylation is also obtained during conversion with trialkyloxonium tetrafluoroborate in inert solvents, such as methylene chloride. The reaction with diazomethane or trimethylsilyldiazomethane in solvents such as methanol or toluene, preferably in mixtures thereof, at temperatures up to the boiling point of the solvent, but preferably at room temperature, mixtures that consist of N- and O-alkyl derivatives are obtained. The methods make possible a selective alkylation of the pyridone relative to benzoic acid amide.

The isomer mixtures can be separated into enantiomers or E/Z isomers according to commonly used methods, such as, for example, crystallization, chromatography or salt formation.

The production of salts is carried out in the usual way, by a solution of the compound of formula I being mixed with the equivalent amount or an excess of a base or acid, which optionally is in solution, and the precipitate being separated or the solution being worked up in the usual way.

The following examples explain the production of the selective compounds according to the invention.

EXAMPLE 1

N-[2-Oxo-2H-1-benzopyran-3-yl-]-2-[(4-pyridyl)methyl]amino-benzoic acid amide 1. 484 mg of 3-amino-2-oxo-2H-1-benzopyran is introduced into 20 ml of methylene chloride. While being cooled with ice, 0.42 ml of triethylamine and 0.40 ml of 2-nitrobenzoyl chloride are added in drops. It is stirred for 4 hours at room temperature, the solvent is distilled off, the residue is taken up with sodium bicarbonate solution, and the product is suctioned off. 0.88 g of N-[2-oxo-2H-1-benzopyran-3-yl-]-2-nitrobenzoic acid amide is obtained. 3-Amino-2-oxo-2H-1-benzopyran was produced according to Bonsignore and Loy, J. Heterocyclic Chem., 35, 117 (1998) from 2-oxo-2H-1-benzopyran-3-carboxylic acid (J. Org. Chem., 64, 1033–1035 (1999)).

2. 880 mg of N-[2-oxo-2H-1-benzopyran-3-yl-]-2-nitrobenzoic acid amide is introduced into 30 ml of ethanol under nitrogen and mixed with 11 ml of cyclohexene and 176 mg of palladium hydroxide on carbon, and it is stirred for 2 hours at 110° C. The catalyst is filtered off, and the filtrate is concentrated by evaporation almost to the dry state. The product is suctioned off. 593 mg of N-[2-oxo-2H-1-benzopyran-3-yl-]-2-aminobenzoic acid amide is obtained.

3. 645 mg of N-[2-oxo-2H-1-benzopyran-3-yl-]-2-aminobenzoic acid amide in 50 ml of methanol and 170 ml of glacial acetic acid are introduced at room temperature and mixed with 0.38 ml of 4-pyridine carbaldehyde. The mixture is stirred for 15 hours and then mixed with 206 mg of sodium cyanoborohydride. It is stirred for 24 hours, and the crystals are suctioned off. The crystals are mixed with 70 ml of methanol, 40 ml of glacial acetic acid and 95 □l of 4-pyridine carbaldehyde and stirred for 48 hours. 57 mg of sodium cyanoborohydride is added and stirred for 15 hours. The product is suctioned off, washed with methanol and dried. 521 mg of N-[2-oxo-2H-1-benzopyran-3-yl-]-2-[(4-pyridyl)methyl]amino-benzoic acid amide with a melting point of 195–197° C. is obtained.

EXAMPLE 2

N-(6-Chloroindazol-5-yl)-2-[(4-pyridyl)methyl]amino-benzoic acid amide 194 mg (0.85 mmol) of 2-(4-pyridylmethyl)aminobenzoic acid is mixed in 8 ml of dimethylformamide with 283 mg (1.69 mmol) of 5-amino-6-chloroindazole. Under argon and in a moisture-free environment, 215 mg (2.13 mmol) of N-methylmorpholine and 386 mg (1.02 mmol) of O-(7-azabenzotriazol-1-yl)-1,1,3,3-tetramethyluronium hexafluorophophate are added to this solution. This mixture is stirred for 4 hours at room temperature. It is then diluted with about 40 ml of water and extracted three times with 30 ml of ethyl acetate each. The combined organic phase is washed with water, dried, filtered and concentrated by evaporation. The residue is chromatographed on silica gel with methylene chloride:ethanol-10:1 as an eluant. 97 mg (30.2% of theory) of N-(6-chloroindazol-5-yl)-2-[(4-pyridyl)methyl]amino-benzoic acid amide with a melting point of 222.8° C. is obtained.

Similarly produced are:

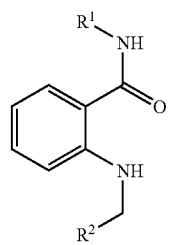

| Example | $R^1$ | $R^2$ | $R^3$ | Melting Point ° C. |
|---|---|---|---|---|
| 3 | 7-methyl coumarin | 4-Pyridyl | H | 191.2 |
| 4 | coumarin | 4-methyl-2-pyridone | H | 232–234 |
| 5 | 7-methoxy coumarin | 4-Pyridyl | H | 171–172 |
| 6 | 6-chloro coumarin | 4-Pyridyl | H | 182–184 |
| 7 | 6-bromo coumarin | 4-Pyridyl | H | 198–200 |

-continued
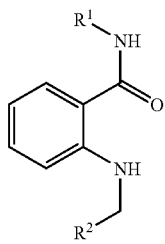
| Example | R¹ | R² | R³ | Melting Point ° C. |
|---|---|---|---|---|
| 8 | 6-methoxy-coumarin-3-yl | 4-Pyridyl | H | 185–187 |
| 9 | 5-methyl-1H-indazol-6-yl | 4-Pyridyl | H | Resin |
| 10 | 5-chloro-1H-indazol-6-yl | 4-Pyridyl | H | 236.7 |
| 11 | 6-methyl-1H-indazol-5-yl | 4-Pyridyl | H | 224.2 |
| 12 | 4-fluoro-2-methylphenyl | 4-Pyridyl | H | Resin |
| 13 | 2-methoxy-5-(trifluoromethyl)phenyl | 4-Pyridyl | H | 135 |
| 14 | 2-chloro-5-(trifluoromethyl)phenyl | 4-Pyridyl | H | 105 |
| 15 | 2-fluoro-5-(trifluoromethyl)phenyl | 4-Pyridyl | H | Resin |

-continued

| Example | R¹ | R² | R³ | Melting Point ° C. |
|---------|-----|-----------|----|---------------------|
| 16 | 2-F, 5-CF₃-phenyl | 4-Pyridyl | F | |
| 17 | 2,5-bis(CF₃)-phenyl | 4-Pyridyl | H | 68 |
| 18 | 2-CF₃, 5-Cl-phenyl | 4-Pyridyl | H | |
| 19 | 2-F, 5-Cl-phenyl | 4-Pyridyl | H | |
| 20 | 2-Br, 5-Cl-phenyl | 4-Pyridyl | H | |
| 21 | 2-CN, 5-Cl-phenyl | 4-Pyridyl | H | |
| 22 | 2,5-diCl-phenyl | 4-Pyridyl | H | |
| 23 | 2-CH₃, 5-Cl-phenyl | 4-Pyridyl | H | |
| 24 | 2-OCF₃, 5-Cl-phenyl | 4-Pyridyl | H | |

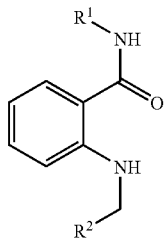

| Example | R¹ | R² | R³ | Melting Point °C. |
|---|---|---|---|---|
| 25 | 2-(hydroxymethyl)-5-chlorophenyl | 4-Pyridyl | H | |
| 26 | 4-bromoisoquinolin-3-yl | 4-Pyridyl | H | 135.8 |
| 27 | 4-bromoisoquinolin-3-yl | 4-Pyridyl | F | |
| 28 | 6-chloro-3-methylquinolin-2-yl | 6-hydroxypyridin-3-yl | H | 172 |

The sample applications below explain the biological action and the use of the selective compounds according to the invention.

Solutions Required for the Tests

Stock solutions
Stock solution A: 3 mmol of ATP in water, pH 7.0 (−70° C.)
Stock solution B: g-33P-ATP 1 mCi/100 μl
Stock solution C: poly-(Glu4Tyr) 10 mg/ml in water Solution for Dilutions
Substrate solvent: 10 mmol of DTT, 10 mmol of manganese chloride, 100 mmol of magnesium chloride
Enzyme solution: 120 mmol of tris/HCl, pH 7.5, 10 μM of sodium vanadium oxide Sample Application 1

Inhibition of the KDR Kinase Activity in the Presence of the Compounds According to the Invention In a microtiter plate (without protein binding) that tapers to a point, 10 μl of substrate mix (10 μl of volume of ATP stock solution A+25 μCi of g-33P-ATP (about 2.5 μl of stock solution B)+30 μl of poly-(Glu4Tyr) stock solution C+1.21 ml of substrate solvent), 10 μl of inhibitor solution (substances corresponding to the dilutions, 3% DMSO in substrate solvent as a control) and 10 μl of enzyme solution (11.25 μg of enzyme stock solution (KDR or FLT-1 kinase) are added at 4° C. in 1.25 ml of enzyme solution (dilute). It is thoroughly mixed and incubated for 10 minutes at room temperature. Then, 10 μl of stop solution (250 mmol of EDTA, pH 7.0) is added, mixed, and 10 μl of the solution is transferred to a P 81 phosphocellulose filter. Then, it is washed several times in 0.1 M phosphoric acid. The filter paper is dried, coated with Meltilex and measured in a microbeta counter.

The IC50 values are determined from the inhibitor concentration that is necessary to inhibit the phosphate incorporation to 50% of the uninhibited incorporation after removal of the blank reading (EDTA-stopped reaction).

The results of the kinase inhibition IC50 in μM are presented in the table below.

Sample Application 2

C-Kit-Isolated Kinase-Inhibition Test

| Stock solutions: | |
|---|---|
| 10x solvent: | 400 mmol of trisHCl, pH 7.5; 10 mmol of DTT, 10 mmol of manganese chloride, 100 mmol of 2.5% polyethylene glycol |
| Magnesium chloride, 20,000 inhibitors: | 2 mmol in dimethyl sulfoxide |
| Substrate-stock solution: | 3 mg/ml of poly(Glu4Tyr)n Sigma P275 in water, frozen portions |
| ATP-stock solution: | 37.5 μM of ATP in water, set at pH 7.5 and frozen portions. |
| 100x vanadate solution; | 1 mmol of sodium vanadate in water |
| Stop solution: | 250 mmol of ethylenetetraaminoacetic acid (EDTA), pH 7.0 |
| Filter/washing solution: | 0.5% phosphoric acid |

Assay Solutions

Substrate Solutions for 125 Assays:

10 μl of ATP (37.5 μM), 25 μCi of γ33P-ATP (~+2.5 μl of Amersham redivue solution) and 10 μl of poly-(glu,tyr) are mixed with 1.23 ml of solvent (1×).

Inhibitor Solution:

The compounds are brought to the desired concentration in the solvent (1×).

Enzyme Solution:

The corresponding enzymatic preparation is brought to the necessary concentration with the solvent (1×) to obtain 1.24 ml. Then, 12.5 μl of sodium vanadate solution is added.

Assay

The components are added in the following sequence to a microtiter plate with round or stippled floors:

10 μl of the inhibitor in 3× final concentration,
10 μl of substrate mixture, said components are mixed, and the reaction is started by adding:

10 μl of enzyme preparation.

The batch is incubated for 10 minutes and then brought to a halt by adding 10 μl of stop solution. 10 μl of the thus treated batch is added to the phosphocellulose filter, rewashed in phosphoric acid, then dried and then melted in a meltilex scintillator and measured.

| Example | KDR IC50 (μmol/l) | C-Kit IC50 (μmol/l) |
|---|---|---|
| 1 | 0.003 | 6 |
| 2 | 0.2 | >10 |
| 3 | 0.03 | 8 |
| 4 | 0.03 | >10 |
| 5 | 0.01 | >10 |
| 6 | 0.2 | 10 |
| 7 | 0.2 | >10 |
| 9 | 0.04 | 10 |
| 10 | 0.01 | >10 |
| 11 | 1 | >10 |
| 13 | 0.05 | 5 |
| 14 | 0.001 | 5 |
| 15 | 0.002 | 2 |
| 17 | KH | >10 |
| 26 | 0.001 | 2 |

-continued

| Example | KDR IC50 (μmol/l) | C-Kit IC50 (μmol/l) |
|---|---|---|
| 28 | 0.05 | 0.5 |
| 29 | 0.2 | >10 |
| 30 | 0.02 | 10 |

The invention claimed is:

1. A compound of the formula I:

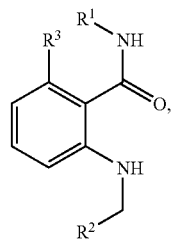

in which

R$^1$ is:

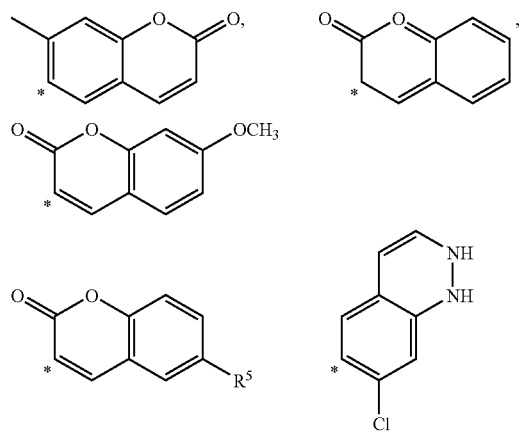

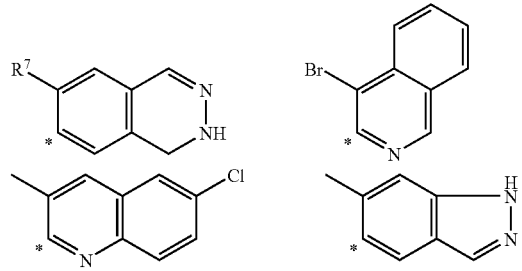

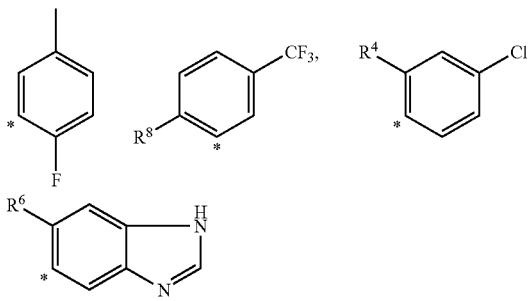

in which:
R⁴ is fluorine, chlorine, bromine, —CF₃, —C≡N, CH₃—, —OCF₃ or —CH₂OH,
R⁵ is chlorine, bromine or OCH₃,
R⁶ is —CH₃ or chlorine,
R⁷ is CH₃ or chlorine,
R⁸ is CH₃, fluorine, chlorine, or CF₃, and
the * indicates the point of attachment of the R¹ group;
R² is pyridyl or the group

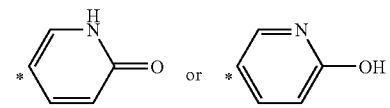

where the * indicates the point of attachment of the R² group, and
R₃ is hydrogen or fluorine;
or a pharmaceutically acceptable salt of a compound of formula I.

2. A method for making a pharmaceutical composition which comprises formulating at least one compound of claim 1 with at least one pharmaceutically suitable, organic or inorganic inert carrier material.

3. A pharmaceutical composition which comprises at least one compound according to claim 1 and at least one pharmaceutically suitable, organic or inorganic inert carrier material.

4. A compound of formula I of claim 1, which compound is selected from the group consisting of:
N-[2-Oxo-2H-1-benzopyran-3-yl-]-2-[(4-pyridyl)methyl]amino-benzoic acid amide, N-(6-Chloroindazol-5-yl)-2-[(4-pyridyl)methyl]amino-benzoic acid amide, and the compounds wherein R¹, R² and R³ are as follows:

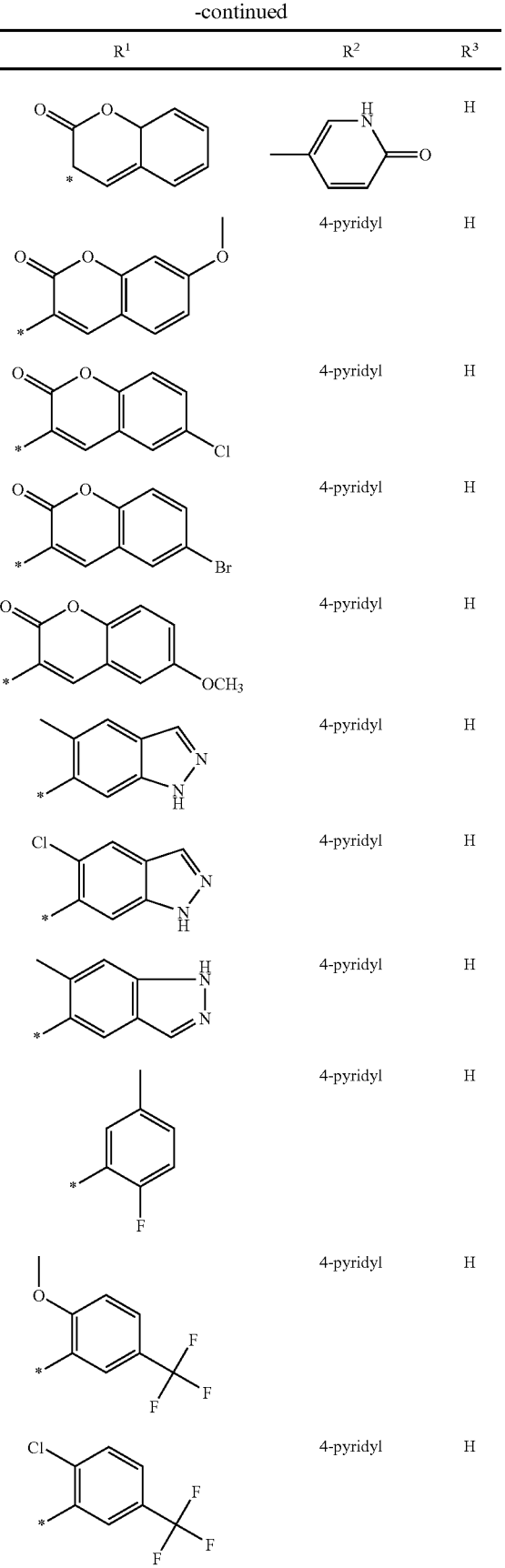

-continued
| R¹ | R² | R³ |
|---|---|---|
| 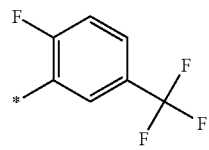 | 4-pyridyl | H |
| 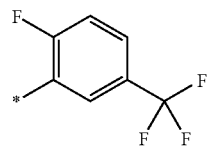 | 4-Pyridyl | F |
| 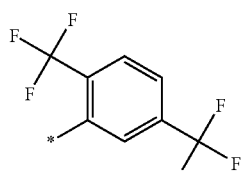 | 4-pyridyl | H |
| 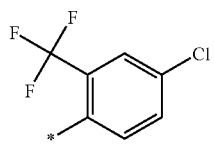 | 4-pyridyl | H |
| 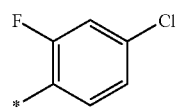 | 4-pyridyl | H |
| 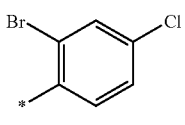 | 4-pyridyl | H |
| 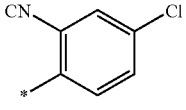 | 4-pyridyl | H |
| 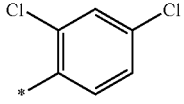 | 4-pyridyl | H |
-continued
| R¹ | R² | R³ |
|---|---|---|
| 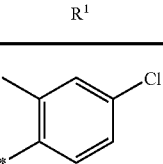 | 4-pyridyl | H |
| 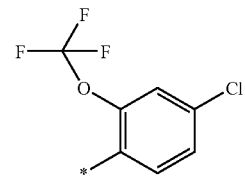 | 4-pyridyl | H |
| 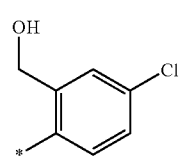 | 4-pyridyl | H |
| 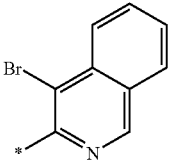 | 4-pyridyl | H |
| 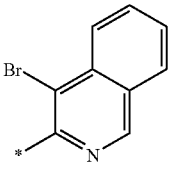 | 4-pyridyl | F |
| 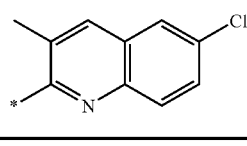 | | H |
where the * indicates the point of attachment of the R¹ group.
* * * * *

UNITED STATES PATENT AND TRADEMARK OFFICE
CERTIFICATE OF CORRECTION

PATENT NO. : 7,081,468 B2  Page 1 of 2
APPLICATION NO. : 10/275480
DATED : July 25, 2006
INVENTOR(S) : Martin Krueger et al.

It is certified that error appears in the above-identified patent and that said Letters Patent is hereby corrected as shown below:

Column 10, line 27 reads

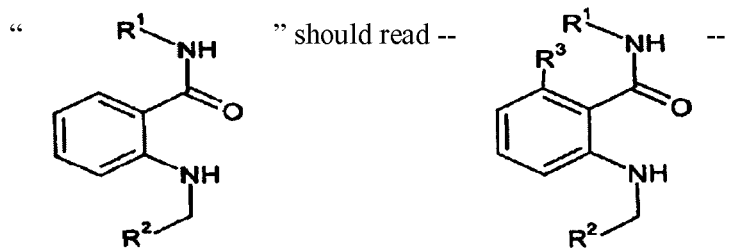

Column 10, Example 4 reads

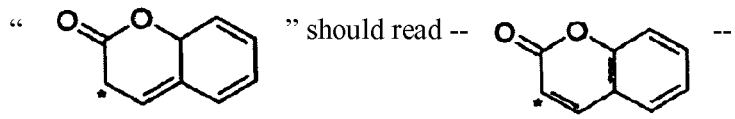

Column 11, line 1 reads

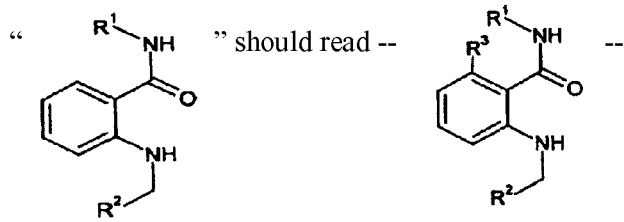

Column 13, line 1 reads

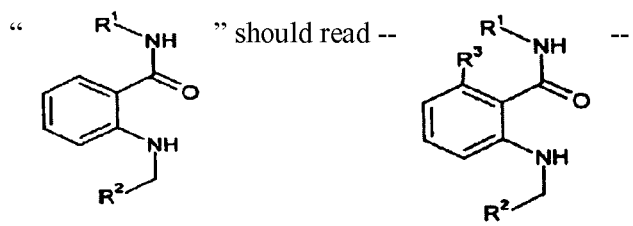

UNITED STATES PATENT AND TRADEMARK OFFICE
CERTIFICATE OF CORRECTION

PATENT NO. : 7,081,468 B2
APPLICATION NO. : 10/275480
DATED : July 25, 2006
INVENTOR(S) : Martin Krueger et al.

It is certified that error appears in the above-identified patent and that said Letters Patent is hereby corrected as shown below:

Column 15, line 1 reads

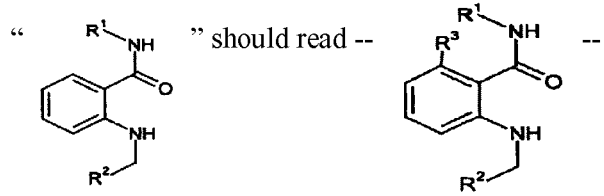

Column 18, line 35 reads

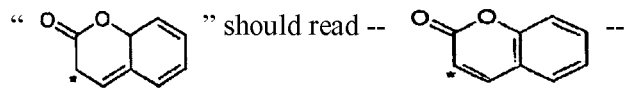

Column 20, line 1 reads

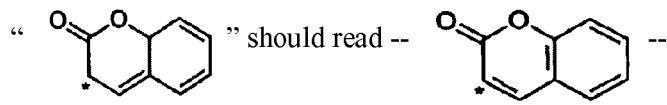

Signed and Sealed this

Sixth Day of May, 2008

JON W. DUDAS
*Director of the United States Patent and Trademark Office*